United States Patent
Kao et al.

(10) Patent No.: US 8,152,809 B1
(45) Date of Patent: Apr. 10, 2012

(54) FLAT CUT BIT FOR CRANIAL PERFORATOR

(75) Inventors: Changqing Chris Kao, Brentwood, TN (US); Peter E. Konrad, Old Hickory, TN (US); Gilbert G. Humbert, Jr., Columbia, TN (US)

(73) Assignee: Vanderbilt University, Nashville, TN (US)

( * ) Notice: Subject to any disclaimer, the term of this patent is extended or adjusted under 35 U.S.C. 154(b) by 994 days.

(21) Appl. No.: 11/452,513

(22) Filed: Jun. 14, 2006

Related U.S. Application Data (60) Provisional application No. 60/690,791, filed on Jun. 15, 2005.

(51) Int. Cl.
| | |
|---|---|
| *A61B 17/00* | (2006.01) |
| *B23B 51/00* | (2006.01) |
| *B23G 5/00* | (2006.01) |
| *B23D 77/00* | (2006.01) |
| *B27G 15/00* | (2006.01) |

(52) U.S. Cl. .......................................... 606/80; 408/202
(58) Field of Classification Search .................... 606/80, 606/96, 79, 84, 82; 408/30, 139, 201, 202, 408/213, 214, 223, 227
See application file for complete search history.

(56) References Cited

U.S. PATENT DOCUMENTS

| | | | | | |
|---|---|---|---|---|---|
| 930,477 | A | * | 8/1909 | Hudson | 606/172 |
| 3,266,345 | A | * | 8/1966 | Weisner et al. | 408/201 |
| 4,273,117 | A | * | 6/1981 | Neuhauser | 606/80 |
| 4,600,006 | A | | 7/1986 | Baker | |
| 4,699,550 | A | | 10/1987 | Baker | |
| 4,803,982 | A | | 2/1989 | Baker | |
| 4,884,571 | A | | 12/1989 | Baker | |
| 4,951,690 | A | | 8/1990 | Baker | |
| 5,007,911 | A | | 4/1991 | Baker | |
| 5,071,295 | A | * | 12/1991 | Greig | 279/156 |
| 5,135,532 | A | | 8/1992 | Baker | |
| 5,180,384 | A | * | 1/1993 | Mikhail | 606/80 |
| 5,252,009 | A | * | 10/1993 | Bossler | 408/145 |
| 5,254,005 | A | * | 10/1993 | Zuest | 433/173 |
| 5,336,226 | A | * | 8/1994 | McDaniel et al. | 606/79 |
| 5,941,706 | A | * | 8/1999 | Ura | 433/165 |
| 5,976,143 | A | * | 11/1999 | McCue | 606/80 |
| 6,120,507 | A | * | 9/2000 | Allard et al. | 606/80 |
| 6,221,076 | B1 | * | 4/2001 | Albrektsson et al. | 606/80 |

(Continued)

OTHER PUBLICATIONS http://www.acracut.com/reuseableperforators.htm, Acra-Cut, pp. 1 to 4, Mar. 24, 2005.

(Continued)

*Primary Examiner* — Thomas C. Barrett
*Assistant Examiner* — David Bates
(74) *Attorney, Agent, or Firm* — Wyatt, Tarrant & Combs, LLP (57) ABSTRACT

Described herein is a cranial surgery drill bit having a safety self stopping mechanism for use on bone material to prevent or repair skin erosion and infection which may result from the placement of a cap for holding the lead from Deep Brain Stimulation surgery. The surgical procedure of attaching a lead holding cap onto the bone material of a skull requires an attachment which results in no movement of the lead. Accordingly, counter boring the skull surrounding a pre-existing perforation bore so that the cap is not significantly above the surface of the skull is a technique which allows the cap user to brush hair, etc., without disrupting the attachment and placement of the lead.

15 Claims, 7 Drawing Sheets

U.S. PATENT DOCUMENTS 6,884,246 B1 * 4/2005 Sonnabend et al. ............ 606/80
7,344,540 B2 * 3/2008 Smucker et al. ................ 606/87
7,399,303 B2 * 7/2008 Michelson ...................... 606/79

OTHER PUBLICATIONS http://www.acracut.com/disposableperforators.htm, Acra-Cut, pp. 1 to 4, May 18, 2005.

http://www.coromant.sandvik.com/sandvik/1810/Internet/se02728.nsf/Alldocs/Products*Milling*Facemilling, Sandvik Coromant, p. 1 of 1, May 18, 2005.

http://www.bamanufacturing.com/images/anatomy—wood.jpg, carbide cutting tip, flute, drive shank, lead screw, spur, p. 1 of 1, May 18, 2005.

http://www.tpub.com/steelworker2/121.htm, Drill Bits, Integrated Publishing, p. 1 of 6, Jun. 15, 2005.

http://www.constructionmaintenance.org/id681—m.htm, Chptr 7 Lathes, General Purpose Cutting Tools, Single Point Tool Bits, Angles of Tool Bits, p. 1 of 5, Jun. 15, 2005.

* cited by examiner

FLAT CUT BIT FOR CRANIAL PERFORATOR

This application claims the benefit of U.S. Provisional Patent Application No. 60/690,791, filed Jun. 15, 2005, entitled "Flat Cut Bit for a Cranial Perforator," which is hereby incorporated by referenced in its entirety.

Be it known that we, Changqing Chris Kao, a United States citizen, residing at 554 Lester Court, Brentwood, Tenn. 37027, Peter E. Konrad, a United States citizen, residing at 345 Harbour Drive, Old Hickory, Tenn. 37138, and Gilbert G. Humbert Jr. a United State citizen, residing at 1653 Carters Creek Pike, Columbia, Tenn. 38401, have invented a new and useful "Flat Cut Bit for Cranial Perforator."

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to a drill bit for cranial surgery, particularly for a cranial perforator.

BACKGROUND OF THE INVENTION

Deep Brain Stimulation (DBS) has become a technique for the treatment of movements disorders such as Parkinson's, essential tremor and dystonia as well as obsessive compulsive disorders and epilepsy. DBS has replaced thalamotomy or lesioning, and pallidotomy as a procedure in the last four to five years. It has proved very effective and as a procedure, has been recognized by the FDA. At the present, the cost of surgery and implants is extremely expensive (as much as $80,000 for bilateral implants), however it does improve the quality for life for patients and gives them an ability to be independent. Alternative procedures for the above identified tremor disorders include neuronal transplantation and growth factor infusion, though these procedures have not yet produced the clinical results as has DBS.

One of the critical steps during DBS surgery is locking of the head in a stereotactic headframe for locating the lead at the final position of the electrode implantation. Several hours of cranial mapping lead to the selection of this site, which is critical to the success of the procedure. In order to assure accurate location and adequate locking of the electrode on the cranium, the periphery around the cranial punch must be carefully prepared such that the plastic cap housing the connection has an absolutely concurrent contact with the skull at the site. Manual preparation of the surface is time consuming and irreparable damage of the skull is a continuing concern. Manual preparation requires repetitive test mounting of the electrode cap, which requires precious time and components are not infrequently accidentally dropped, further adding to the delay and cost. The present invention enables a quick, precise preparation of the surgical site, overcoming the need for test mounting, lost time and lost parts, while delivering predictable stability to the electrode fixation. The inventive drill bit assures a planar surface around the burr hole on the curved, irregular skull surface. By providing the enhanced cranial base and cap mounting in the DBS procedure prevents skin erosion due to cap/lead extrusion. Often such extrusion causes infection and may result in the later extraction of the cap and lead. Further, the optimized mount of the cap and lead ensures a smooth layer of skin over the cap and an enhanced cosmetic effect.

Representative devices for performing the cranial perforation are as follows. Each listed document is hereby incorporated herein in its entirety.

U.S. Pat. No. 5,135,532 for a Drill Head Assembly for Cranial Perforators illustrating inventive cutting flutes;

U.S. Pat. No. 5,007,911 for a Drill Head Assembly for Cranial Perforators illustrating particular drill head construction and drive mechanism;

U.S. Pat. No. 4,951,690 for a method of drilling through bone structure;

U.S. Pat. No. 4,884,571 for a cranial perforator with a reentrant cutting segment;

U.S. Pat. No. 4,803,982 for an improved camming structure for a cranial perforator drive;

U.S. Pat. No. 4,699,550 for a safety disengagement mechanism for a cranial drill to prevent over drilling; and U.S. Pat. No. 4,600,006 for a drill bit including an inner and outer drill mechanism and a clutch for stopping drilling action.

There is thus a need for a drill bit for cranial perforations having the following characteristics and advantages over existing art.

SUMMARY OF THE INVENTION

The present invention is a disposable drill bit for drilling a recess around an existing perforation bore. During a medical procedure, such as Deep Brain Stimulation, the recess receives a cap which holds an electrode lead which has been placed within the brain. Placing the cap in the recess, or counter bore, prevents skin erosion and injury to the scalp which may result in infection. Accordingly, the present invention discloses a drill bit for cutting bone, such as a skull, the drill bit including a shaft having a first end and a second end, wherein the first end is adapted to engage a drive so that the shaft rotates, a cutting assembly having a plurality of cutting teeth, the cutting assembly attached to the second end of the shaft, wherein the plurality of cutting teeth extend axially and opposite from the first end of the shaft, and a stabilization hub having an end, the stabilization hub fixedly attached to the second end of the shaft, wherein the stabilization hub is an axial protuberance of the shaft extending further axially than the plurality of cutting teeth. In certain embodiments, the cutting assembly is planar and extends radially from the shaft, the first side of the cutting assembly being opposite of the plurality of cutting teeth. In other embodiments, the cutting assembly is a solid planar plate extending radially from the shaft for preventing escape of drilled particles therethrough. In certain embodiments, the plurality of cutting teeth extend a radial length of the cutting assembly in order to define a cutting surface. The stabilization hub has a diameter that is less than the diameter of a perforation bore, so that the stabilization hub engages the perforation bore in order to stabilize the location of the cutting assembly. In certain embodiments, the stabilization hub has a diameter less than about 13.5 mm for engaging a perforation bore in order to stabilize the location of the cutting assembly. In other embodiments, the stabilization hub has a length less than a thickness of a skull, so that the stabilization hub engages only a perforation bore of the skull in order to stabilize the location of the cutting assembly. In still other embodiments, the stabilization hub extends axially from a cutting surface defined by the plurality of cutting teeth a length of from about mm to about 7 mm. The end of the stabilization hub may be flat or rounded. The plurality of cutting teeth may be cutting flutes.

The present invention also discloses a drill bit for cutting bone having a predetermined cutting depth, including, a shaft having a first end and a second end, wherein the first end is adapted to engage a drive so that the shaft rotates, a plurality of cutting teeth defining a cutting surface, each of the plurality having a first end and a second end, each of the first ends fixedly attached to the second end of the shaft, wherein the plurality of cutting teeth extend radially from the shaft, a planar ring having a first surface, the planar ring fixedly attached to each of the second ends of the plurality of cutting teeth so that the first surface of the planar ring contacts a surface of a bone material in order to obstruct further cutting by the plurality of cutting teeth, and a hub fixedly attached to the second end of the shaft, the hub extending axially further than the plurality of cutting teeth, in order to engage a perforation bore in the bone material. The first surface of the planar ring may have an axial position equal to an axial position of the cutting surface, an axial position that is about 1 mm recessed from the cutting surface, or an axial position that is about 2 mm recessed from the cutting surface. In certain embodiments, the plurality of cutting teeth may include only four cutting teeth. In other embodiments, the planar ring may have a diameter of from about 23 mm to about more than 29 mm. In other embodiments, the width of the planar ring is about 2 mm. In still other embodiments, the drilling implement for drilling human bone includes a shank having a first end for interconnection with a driver, wherein the shank has a central hub extending in a direction opposite the first end, a radially extending array of cutting flutes disposed uniformly around the hub, to a predetermined radial extent, wherein the cutting flutes extend axially from the shank a distance less than the extent of the hub.

It is an object of the invention to provide a drill bit for the expedient, repeatable preparation of a recess, or counter bore, surrounding an existing perforation bore for the cranial location of the electrode for Deep Brain Stimulation.

It is another object of the invention to provide drill bit which is compatible with the instrumentation for cranial perforation such that the site of the cranial perforation site may be expediently prepared for the fixation of the plastic cap securing the cranial electrode.

It is another object of the invention to provide a drill bit which expeditiously mills the peripheral site surrounding the pre-existing cranial perforation bore for the immediate attachment of the electrode cap.

It is another object of the invention to provide a method of locating an electrode for performing Deep Brain Stimulation in a more expeditious and uniform manner.

It is another object of the invention to provide a drill bit for milling, or drilling, to a predetermined depth for enhanced safety and to avoid brain injury by drilling too deep during brain surgery.

It is another object of the invention to provide prevention of skin erosion and/or infection control subsequent to Deep Brain Stimulation surgery.

BRIEF DESCRIPTION OF THE DRAWINGS

FIGS. 6A and 6B are perspective views of an alternative embodiment of the inventive bit illustrated in FIG. 1. FIG. 6A shows an alternate cutting surface. FIG. 6B shows that alternate cutting surface surrounded by a planar ring which stops drilling at a predetermined position.

FIGS. 8A and 8B are perspective views of the present invention. Shown in FIG. 8A is another embodiment of the bit illustrated in FIG. 7, showing the planar ring surrounding the bit teeth, thereby allowing the bit to stop drilling at a predetermined position.

FIGS. 12A, 12B, and 12C show a side view of the cranial bit of FIG. 10 with the hub disposed in the pre-existing cranial perforation bore for preparing a counter bore. FIG. 12A shows the steps of drilling a counter bore. FIG. 12B shows a side view of the retaining cap being placed in the site around the cranial perforation prepared as illustrated. FIG. 12C shows a side view of the retaining cap positioned in place.

FIGS. 13A, 13B, and 13C show the steps of placing a cap within a bore when using the embodiment of the cranial bit described in FIG. 11. FIG. 12A shows a side view of the cranial bit of FIG. 11 with the hub disposed in the pre-existing cranial perforation bore for preparing the counter bore. FIG. 12B shows a side view of the retaining cap being placed in the site around the cranial perforation prepared as illustrated. FIG. 12C shows a side view of the retaining cap when positioned in place.

PREFERRED EMBODIMENTS OF THE INVENTION

The present invention discloses a drill bit 2, also called a drilling implement 2, for drilling human bone in order to prepare a recess, or counter bore, for receiving a retainer cap which holds an electrode lead. The drill bit 2 includes a shank 4 having a first end 14 for interconnection with a driver, the shank 4 having a central hub 12 extending in a direction opposite the first end 14, a radially extending array of cutting flutes 10 disposed uniformly around the hub 12, where the cutting flutes 10 extend axially from the shank 4 a distance less than the extent of the hub 12. Another embodiment of the invention disclosed herein is a drill bit 2 including a shaft 4 having a first end 14 and a second end 16, wherein the first end 14 is adapted to engage a drive so that the shaft 4 rotates, a cutting assembly 22 having a plurality of cutting teeth 24, the cutting assembly 22 attached to the second end 16 of the shaft 4, wherein the plurality of cutting teeth 24 extend axially and opposite from the first end 14 of the shaft 4, and a stabilization hub 12 fixedly attached to the second end 16 of the shaft 4, where the stabilization hub 12 is an axial protuberance of the shaft 4 extending further axially than the plurality of cutting teeth 24.

Also disclosed herein is another embodiment of a drill bit for cutting bone, including a shaft 4 having a first end 14 and a second end 16, wherein the first end 14 is adapted to engage a drive so that the shaft rotates, a plurality of cutting teeth 24 defining a cutting surface 8, each of the plurality having a first end 26 and a second end 28, each of the first ends 26 fixedly attached to the second end 16 of the shaft 4, wherein the plurality of cutting teeth 24 extend radially from the shaft 4, a planar ring 30 having a first surface 32, the planar ring 30 fixedly attached to each of the second ends 28 of the plurality of cutting teeth 24 so that during use the first surface 32 of the planar ring 30 contacts a surface 42 of a bone material 40 in order to obstruct further cutting by the plurality of cutting teeth 24, and a hub 12 fixedly attached to the second end 16 of the shaft 4, the hub 12 extending axially further than the plurality of cutting teeth 24, so that the hub 12 is received by a perforation bore 44 in the bone material 40.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
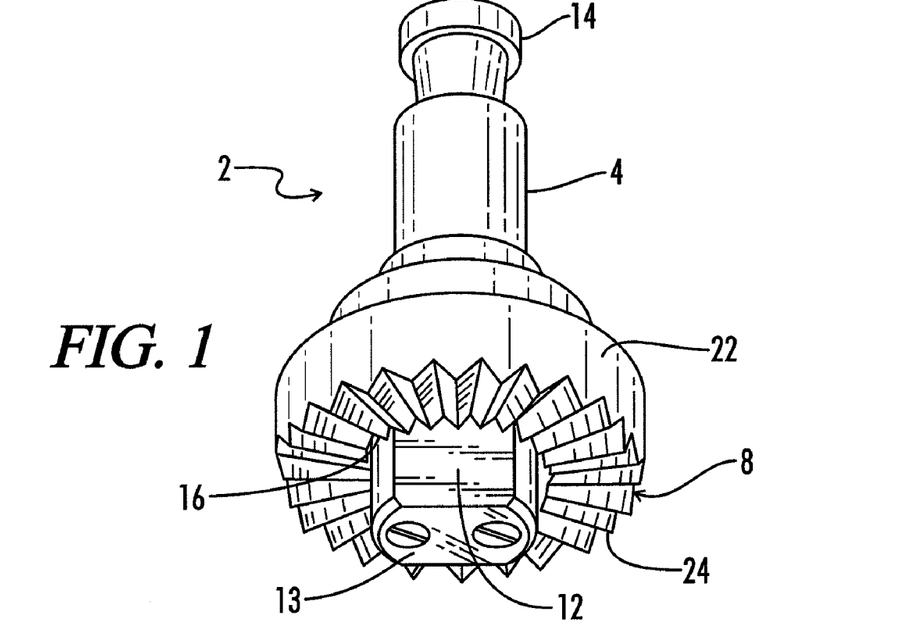
FIG. 1 is a perspective view showing a cranial bit for preparing a mounting boss according to the present invention.

As shown in FIG. 1, the invention is a drill bit 2 having a shank 4, which in the preferred embodiment illustrated is adapted with a shank configuration, also called first end 14 of the shank 4, to be compatible with surgical drilling tools currently in use. Examples of such tools are those manufactured under the ACRA-CUT trademark by the ACRA-Cut corporation of Acton, Mass., one of the leading producers of cranial perforator apparatus. The operative end of the bit 2 includes a cutting surface 8 having thereon radially disposed cutting 10 teeth 24 disposed around hub 12, the hub 12 having an end 13. Alternative arrangements of cutting teeth are illustrated in subsequent figures for alternative embodiments of bits 2. Further, one of ordinary skill in the art is familiar with the specific arrangements of cutting teeth which are desirable for each specific task. To that end, as used herein, "cutting teeth" is a broader term including cutting flutes 10 and other cutting blades, or the like. One of ordinary skill in the art may desire to use any of the many arrangements of cutting teeth which are commercially available.

The bit 2 of the present invention is utilized for preparing the surface of the skull for the mounting of an electrode for the technique known as Deep Brain Stimulation (DBS). The treatment of DBS is to effect a control for tremors that includes the mounting of a stimulating electrode lead into the ventrointermediate nucleus of cells of the thalamus. The lead 34 is connected to a pulse generator (not shown) that is surgically implanted under the skin, usually in the upper chest, not unlike heart stimulating devices. The lead wire 34 is threaded from the pulse generator, generally under the skin, to the scalp where the leads are held in place by a cap 36 and the ends thereof are implanted into the target cells in thalamus. It is imperative that the leads be precisely implanted and subsequently securely mounted on the scalp, lest it be displaced or otherwise allowed to move and compromise its contact with the thalamus.

DBS is becoming the treatment of choice for different tremors since it provides a variety of readily controllable treatments. It has replaced the lesioning procedure (controlled destruction of brain tissue) in use a few years ago. The pulse generator is configured to provide a varied signal that is adapted to the particular type of tremor being treated. The delivered signal may be varied in pulse frequency and width as well as strength, or voltage. Essential tremors generally exhibit a 3 to 4 Hz effect in hand, arm and head tremors whereas, Parkinson's exhibits tremor rigidity, akinesia and dyskinesia. These tremors are generally treated with high frequency stimulation (around 150 Hz). The signal output is tuned to the particular type and nature of the tremor. Likewise, the pulse generator may be activated (turned on and off) by such as a magnetic switch, wherein a simple permanent magnet may be manually passed over the generator, thereby sequencing a switch within the device to change the operating state from "off" to "on", or vice versa. Such control is useful in certain types of treatment, where the tremor is irregularly experienced. Alternatively, in such conditions as Parkinson's, the tremor is generally more continuous such that the switching mode may be less important. Universally important in the use of the technique is that the electrode be absolutely stabilized on the scalp, and that the contact of the lead with the nerve not be compromised.

One of the critical steps in the DBS surgery is the locking of the lead into its final position. This occurs after usually several hours of mapping the nerve structure and neurological examination of the tremor. The therapy is extremely target dependent, in that the location of the implanted lead contacts must be on the nucleus of the targeted brain structures, and, the lead must be secured by such as cap 36 that the targeted position is not later compromised by movement. In location of the lead 34 and fixing it initially, it is imperative that the situs of the fixation of the plastic securing cap 36 be absolutely well-positioned. Accordingly, the site around the perforation bore 44 which has been drilled with such as the ACRA-Cut bit for the implantation of the wire into the thalamus, must be separately prepared for the mounting lock cap 36. This requires a precisely flat, regular counter bore 20, as it were, around the perforation. Previously to our invention, this surface was generally manually prepared, taking precious time in the surgical procedure, and also being very technique sensitive, and thus subject to manual irregularity. More times than preferred, inadvertent damage would occur to the mounting counter bore 20, either because of the manual skill required, the imperfect nature of the tool used or some irregularity of the Site.

Figure 2:
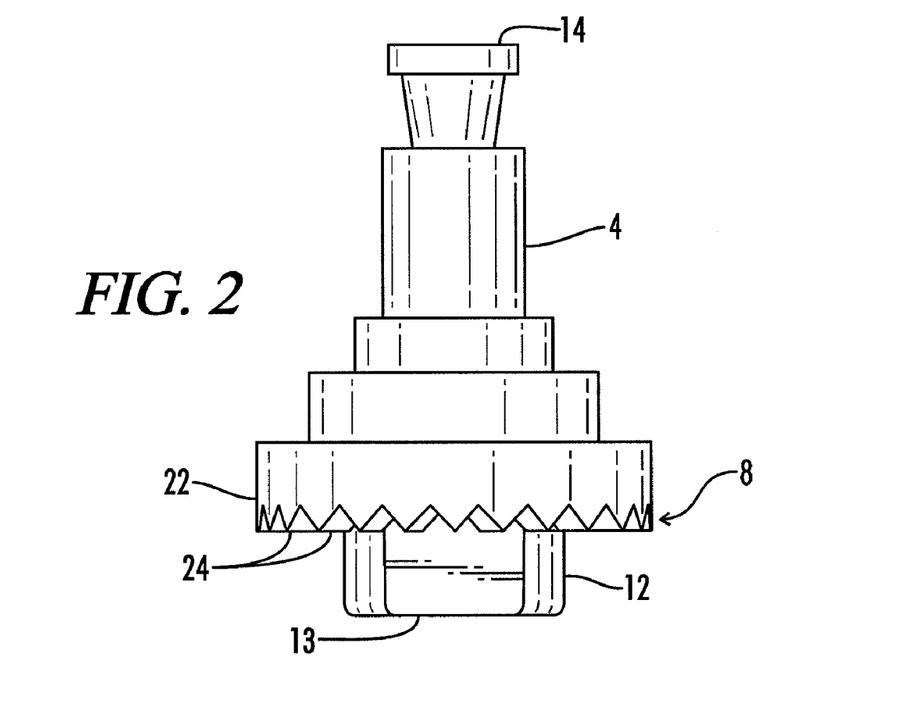
FIG. 2 is side view of the embodiment of the cranial bit illustrated in FIG. 1.
Figure 3:
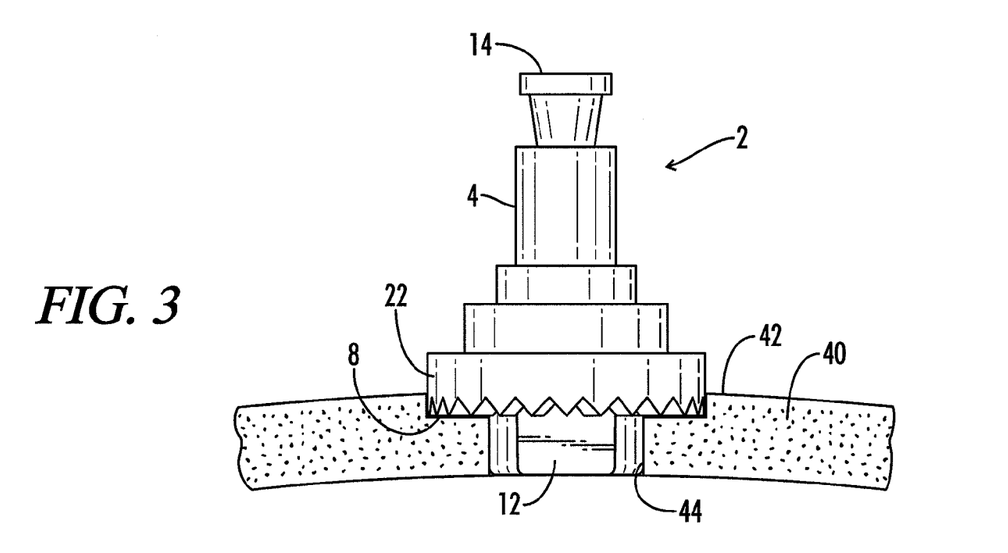
FIG. 3 is a side view of the cranial bit of FIG. 1 disposed in the cranial perforation for preparing the site.
Figures 4, 5:
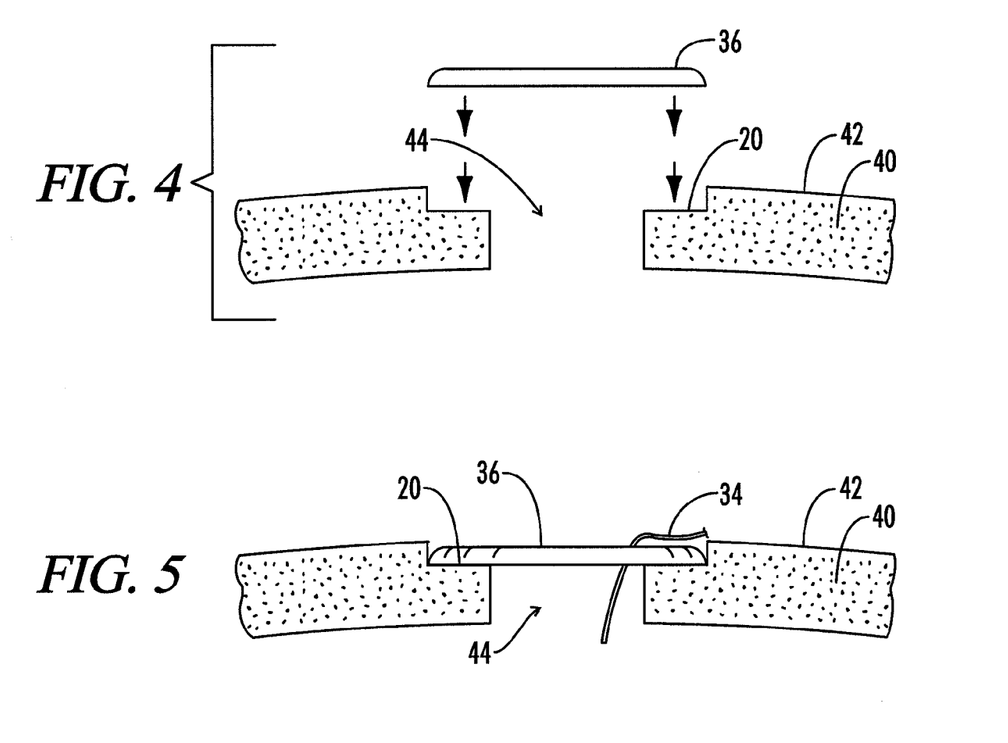
FIG. 4 is a side view of the retaining cap for placement on the site around the cranial perforation prepared as illustrated in FIG. 3.
FIG. 5 is a side view showing the retaining cap illustrated in FIG. 4 in place.

Referring now to FIGS. 3-5, there is shown the steps for drilling a counter bore 20. The drill bit 2 of the present invention has a hub 12 which is received by the cranial perforation bore 44 in order to allow the cutting surface 8 to drill the bone material 40. Shown in FIG. 4 is a diagram of the placement of the cap 36 into the counter bore 20. FIG. 5 shows the cap 36 in the proper position seated on the counter bore 20. Once in place, the cap 36 may be fixed to the skull by fasteners, or the like. Also shown therein is the lead 34 which is held in a fixed position by the cap 36. Regarding the first embodiment of the drill bit 2 shown in FIGS. 1-3, note that safety is built into the design of the bit 2. The cutting assembly 22 is a solid structure which provides only a horizontal route of escape for bone residue being cut away from the bone material 40. The continued presence of the bone residue slows the cutting rate of the bit 2 in order to act as a safety mechanism of slowing the milling, or drilling, in order to prevent the inadvertent drilling of a counter bore 20 which is too deep.

Stated another way, the horizontal route of escape for bone residue, and the build up of bone residue slows the milling, or drilling, so that drilling is not too deep. Obviously, drilling deeper than intended would allow the hub 12 to pass through the perforation bore and could result in brain injury due to hub 12 contact.

Figure 6A:
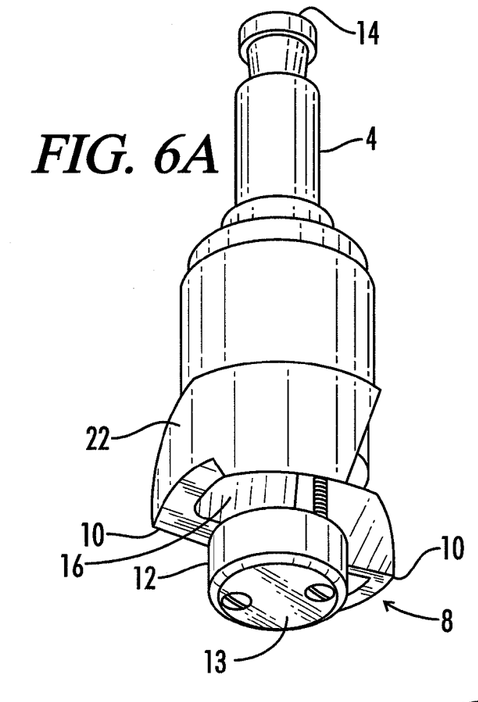
Figure 6B:
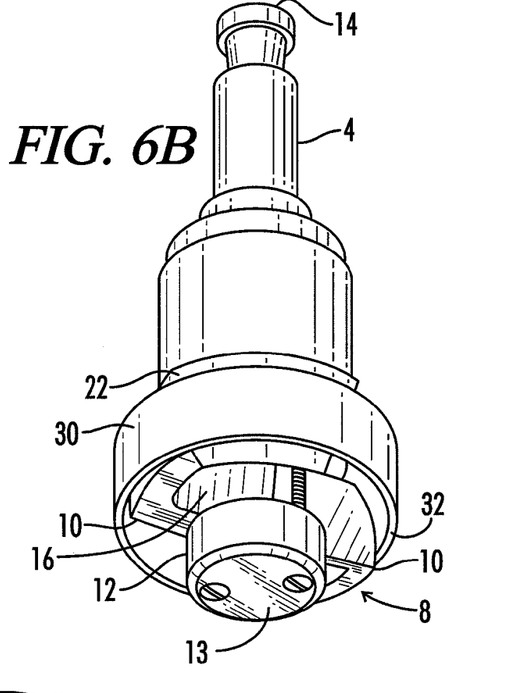
Figure 7:
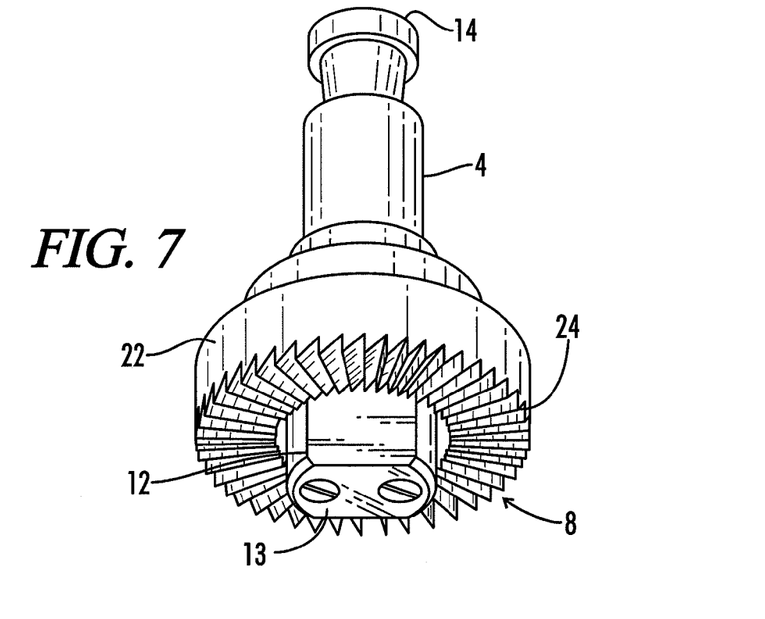
FIG. 7 is a perspective view of still another embodiment of the inventive bit illustrated in FIG. 1, wherein the angle of the leading of the bit teeth are more vertically cut.

Referring now to FIGS. 6A, 6B, and 7, there are shown alternative embodiments of the present invention. Specifically shown in FIGS. 6A and 6B are drill bits 2 having specifically designed cutting surfaces 8. The difference between FIGS. 6A and 6B is that FIG. 6B has a planar ring 30 surrounding the cutting surface. The planar ring 30, is further described below. Referring to FIG. 7, there is shown a drill bit 2 of the present invention having cutting teeth 24 on the cutting surface 8 which are much more vertical in orientation. As stated above, the selection of a specific cutting surface 8 or cutting flutes 10, is dependent upon the specific needs of the surgeon. In alternate embodiments, a surgeon or other professional may make use of a cutting surface 8 which is well known in the art.

Figure 8A:
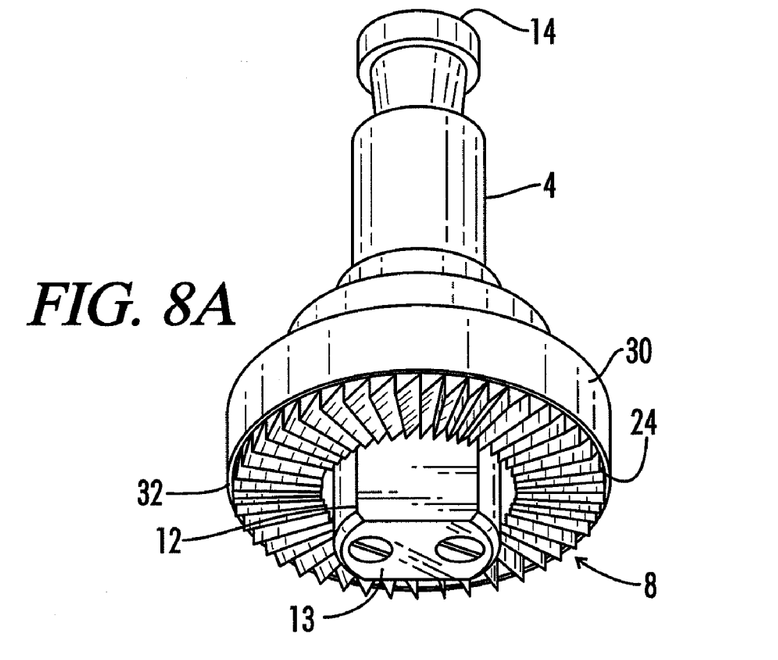

Shown in FIG. 8A is a perspective view of another embodiment of the present invention. Shown in that embodiment is a planar ring 30 which surrounds the cutting surface 8 and the cutting teeth 24. The function of the planar ring 30 is to provide a predetermined cutting depth to the cutting teeth 24. The planar ring 30 acts as a stopping mechanism by contacting the bone material 40 in order to prevent further milling or drilling by the cutting surface 8. Examples of the planar ring 30 functioning in this capacity, in various embodiments of the present invention, are shown in FIGS. 12 and 13, further discussed below. In certain embodiments, the planar ring 30 may be constructed of any rigid material, such as steel, or the like, suitable for the stated function. Those of skill in the art are familiar with the manufacture of bits. As the shank 4 rotates, the cutting surface 8, hub 12, and planar ring 30 rotate simultaneously. The planar ring 30 may have a round, square, or other cross sectional shape, as long as there is a first surface 32 which is relatively planar for contacting the bone material 40 and stopping further milling of said material. In certain embodiments, the planar ring 30 may have a cross sectional width of approximately 2 mm. In certain embodiments, the diameter of the planar ring 30 is greater than the diameter of the counter bore 20 being drilled for the placement of the cap 36.

Those of skill in the art are familiar with the manufacture of bits. As the shank 4 rotates, the cutting surface 8, hub 12, and planar ring 30 rotate simultaneously. The planar ring 30 may have a round, square, or other cross sectional shape, as long as there is a first surface 32 which is relatively planar for contacting the bone material 40 and stopping further milling of said material. In certain embodiments, the planar ring 30 may have a cross sectional width of approximately 2 mm. In certain embodiments, the diameter of the planar ring 30 is greater than the diameter of the counter bore 20 being drilled for the placement of the cap 36.

Figure 8B:
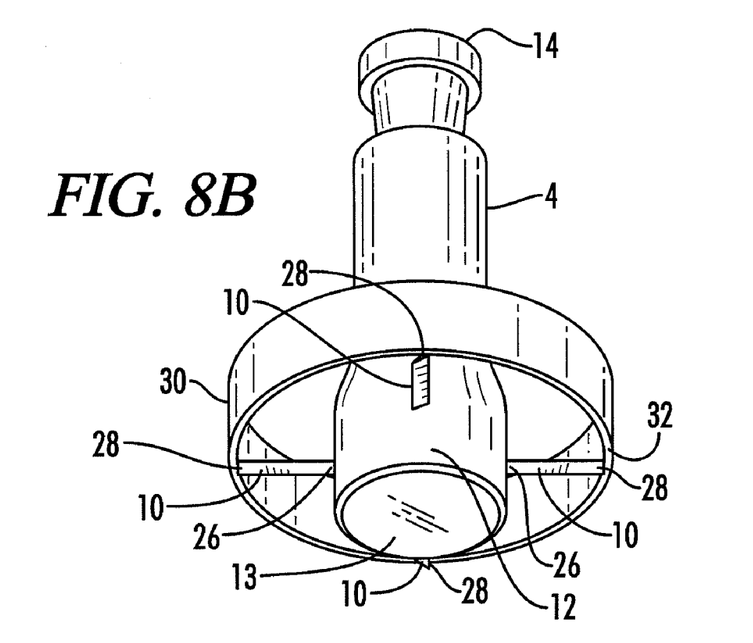
FIG. 8B shows an alternative embodiment of a cranial bit for preparing a mounting boss. Shown there is the planar ring surrounding the cutting blades according to the present invention.

Referring now to FIG. 8B, there is shown another embodiment of the present invention. The drill bit 2 shown there, having the shank 4, also has a cutting surface 8 which includes cutting flutes 10 in a different orientation. As seen in the figure, extending radially from the shank 4 are four cutting flutes 10 which extend so that the second ends 28 of the cutting flutes 10 permanently attach to the planar ring 30. The four blade embodiment of the present invention allows the vertical escape of bone residue which is cut away from the bone material 40. Since the bone residue is easily and quickly expelled, the rate of cutting is quicker. Accordingly, the importance of the planar ring 30 in this embodiment is highlighted as the planar ring 30 provides for a precise stopping point of the drilling when this quick cutting embodiment of the present invention is used. Those of ordinary skill in the art are familiar with the construction of drilling bits having such cutting flutes. The material of construction of such drilling bits are also known to those skilled in the art. By way of example, the non-cutting surfaces may be constructed of stainless steel, while the cutting surfaces may be constructed of a carbon steel, or the like.

Still referring to FIG. 8B, in certain embodiments, the shank 4 has a diameter of 13.5 millimeters, so that the hub 12 may be inserted into the pre-existing perforation bore 44 which typically has a diameter of 14 mm, and the planar ring 30 has a diameter of 29 millimeters. Again, these specific measurements will change as the preferences of those in the art change. Further, depending upon the embodiment of the drill bit 2, the counter bore 20 may have a predetermined depth relative to the planar ring 30 of 0, 1, or 2 millimeters (i.e. the cutting teeth 24 extend beyond the first surface 32 of the planar ring 30 by a predetermined distance). In still other embodiments, the cutting flutes 10 may have an angle of from about 40 to 50 degrees, in order to optimize the cutting process. In certain embodiments, the hub 12 may extend approximately 7 millimeters beyond the cutting surface 8 of the drill bit 2. As mentioned above, the extended hub 12 is received by the perforation bore 44.

Figure 9:
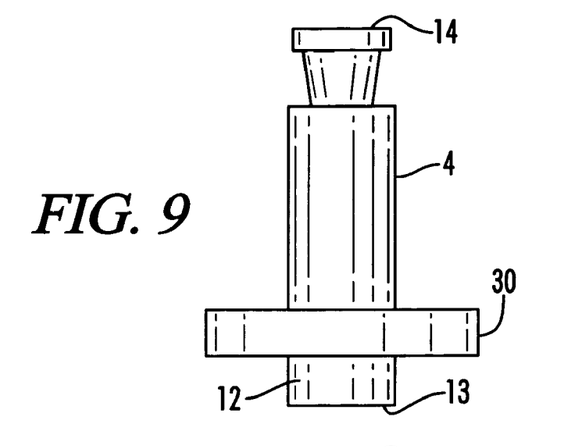
FIG. 9 is a side view of the embodiment of the cranial bit illustrated in FIG. 8. Shown there is the planar ring which is flush with the cutting flutes.
Figure 10:
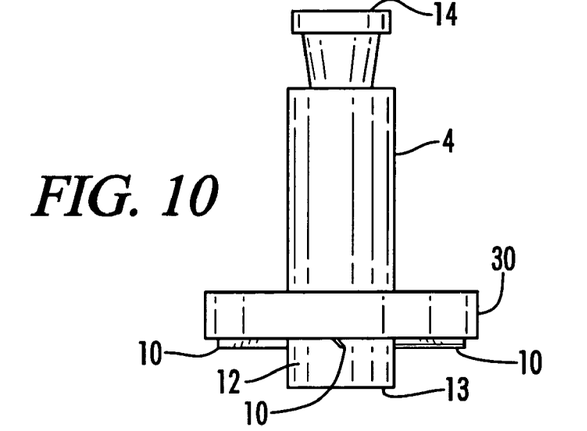
FIG. 10 is a side view of still another embodiment of the cranial bit for preparing a mounting boss according to the present invention. Shown there are the cutting flutes extending in the cutting direction a predetermined distance of approximately 1 millimeter beyond that of the first surface of the planar ring.
Figure 11:
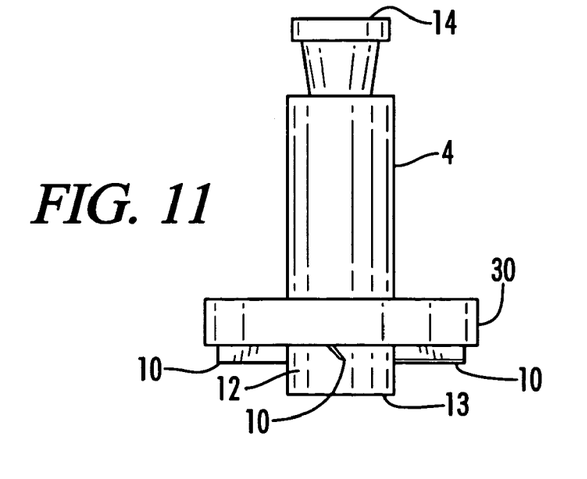
FIG. 11 is a side view of another embodiment of the present invention. Shown there are the cutting flutes extending in the cutting direction a predetermined distance of approximately 2 millimeters beyond the first surface of the planar ring.

Shown in FIG. 9 is an additional embodiment of the present invention in which the cutting surface 8 is flush with the first surface 32 of the planar ring 30. Now referring to the embodiment in FIG. 10, there is shown a drill bit 2 having a cutting surface 8 which extends approximately 1 millimeter further than the first surface 32 of the planar ring 30. In still another embodiment, referring now to FIG. 11, there is shown a drill bit 2 having a cutting surface 8 which extends approximately 2 millimeters further than the first surface 32 of the planar ring 30. Depending upon the size and shape of the cap 36, a user may desire to generate a counter bore 20 having various predetermined depth. Accordingly, those skilled in the art should recognize that these dimensions are adaptable based upon other caps 36 or other devices or instruments which may have different dimensions. Again, this adaptability of the present invention increases its impact on the surgical technique in that it may be used with other surgical devices, and caps 36.

Figure 12A:
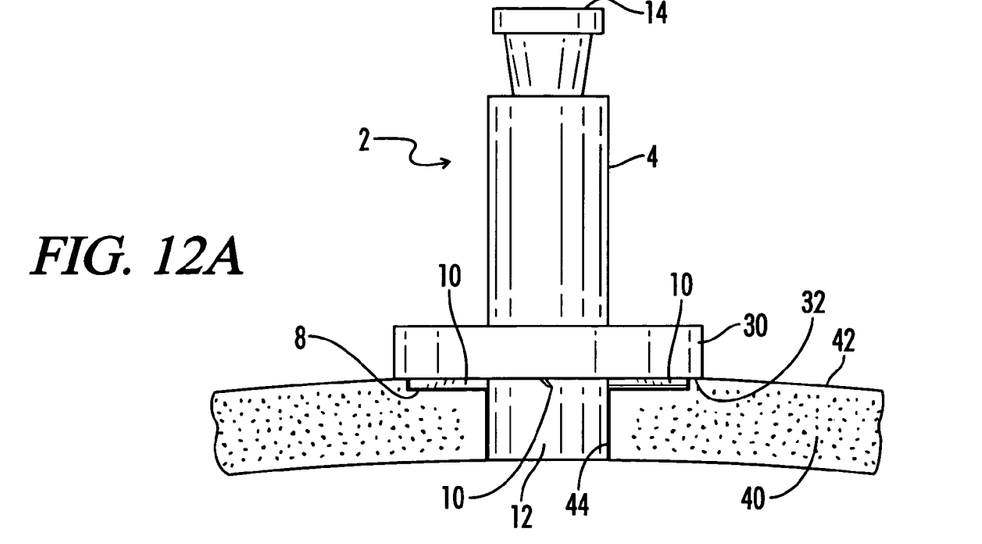
Figure 12B:
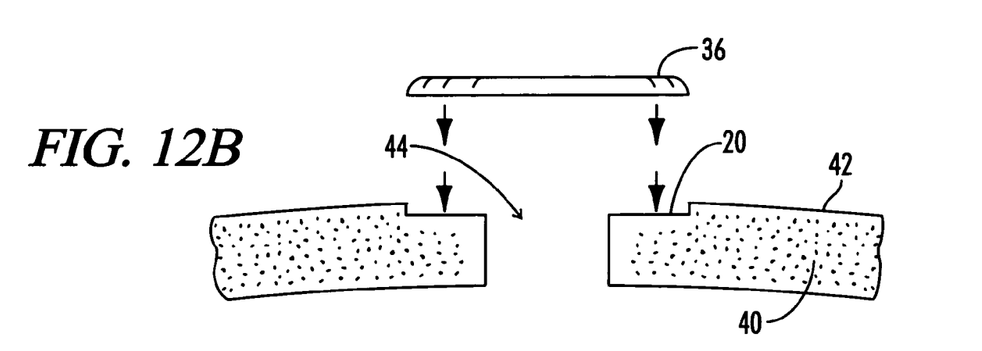
Figure 12C:
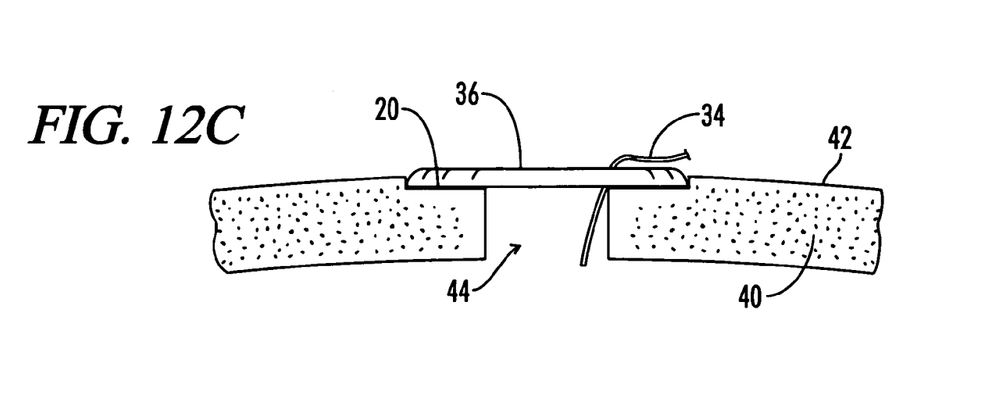
Figure 13A:
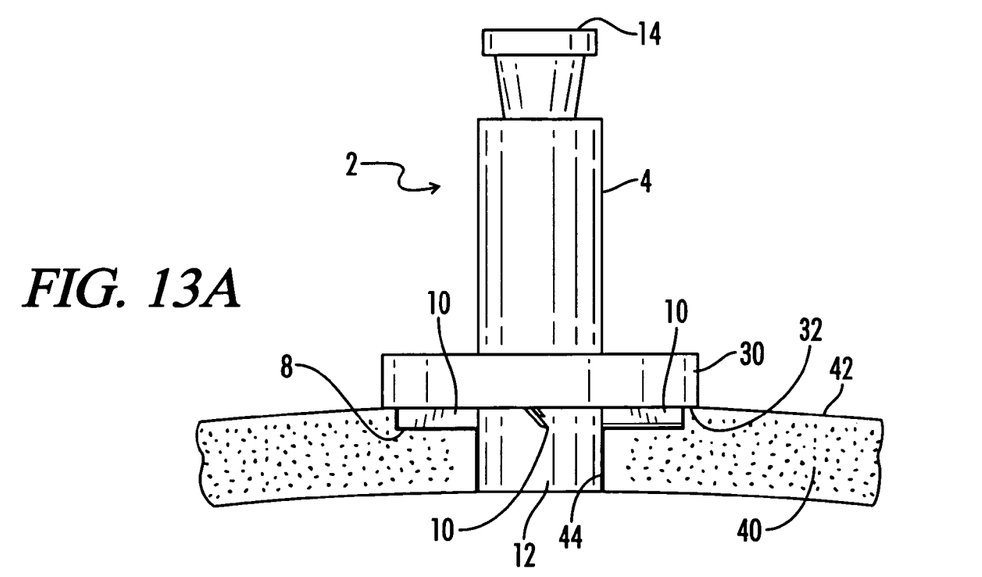
Figure 13B:
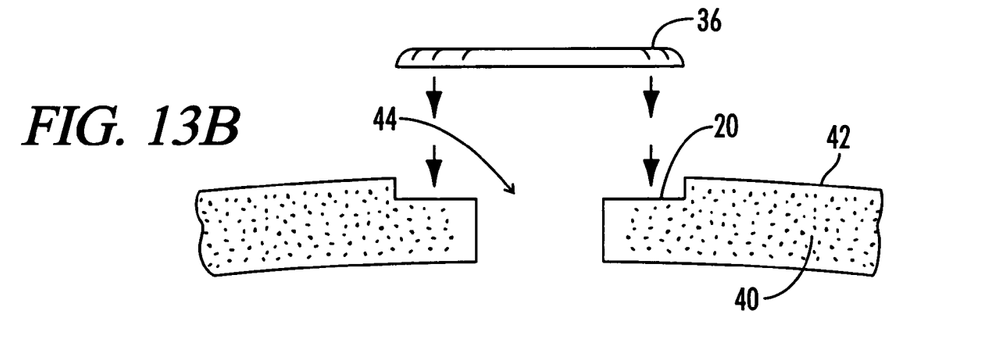
Figure 13C:
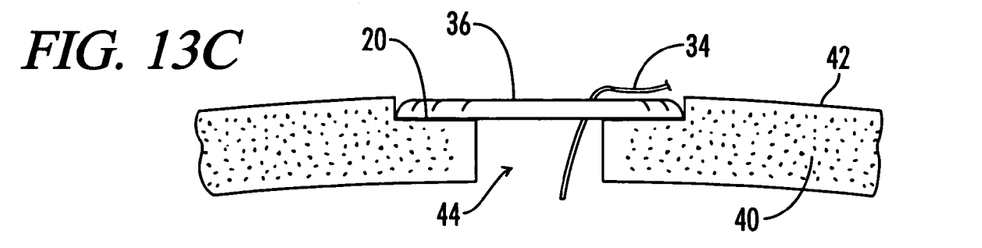

Referring now to FIGS. 12A-12C and 13A-13C, there are shown the surgical steps in using the present invention. Specifically, there is shown drilling of the bone material 40 by the cutting surface 8. Those of ordinary skill in the art know the range of revolutions per minute (rpm) to use to cut bone material 40. In certain embodiments, the drill bit 2 may rotate at approximately 3000 rpm. As best seen in FIGS. 12A and 13A, the first surface 32 of the planar ring 30 is shown to contact the first surface 42 of the bone material 40 in order to prohibit the cutting surface 8 from further progressing into the bone material 40. Stated another way, the planar ring 30 rotates while in contact with the first surface 42 of the bone material 40 as the cutting surface 8 rotates. It is the planar ring's 30 contact with the bone material 40 which prohibits further drilling by the cutting surface 8. Accordingly, it is seen that the difference in extension of the cutting surface 8 beyond that of the first surface 32 of the planar ring 30 results in a counter bore 20 having a specific predetermined depth. Now referring to FIGS. 12B and 13B, there is shown the placement of the cap 36. Such placement results in proper fixation of the lead 34 by the properly placed cap 36, as shown in FIGS. 12C and 13C. FIGS. 13A-13C show an embodiment of the present invention in which the cutting surface 8 extends approximately 2 millimeters further than the first surface 32 of the planar ring 30. Accordingly, the resulting counter bore 20 which results therefrom, has a predetermined depth of 2 millimeters.

The drill bit 2 disclosed herein provides site preparation in seconds as opposed to many minutes. Further, the tool provides a predictability of result that removes most of the element of manual preparation, ensuring a superior counter bore for the mounting of the securing cap 36. In the illustrated embodiments, the bits 2 are adapted with shank ends, also called first ends 14 of shanks 4, that are compatible with rotary tools currently being used in the surgical theater, so only the bit 2 itself must be added to the instrument inventory. Further, as illustrated in the embodiments discussed herein, the bit 2 may be configured with a variety of cutting flutes 10, adapted to the preferences of the surgeon. Particular implanting techniques or bone character may dictate more, or less, aggressive cutting teeth 24. The inventive tool provides a base configuration with the positioning of the hub 12 and radial extent of flutes 10 to ensure the precise positioning of the bore 20, and allows the selection of alternative bits 2 as to the particular cutting teeth 24 preferred.

Referring again to the Figures, the bit 2 disclosed exhibits a cutting flute 10 configuration that might be described as providing a plunge milling or polishing action to the surface of the skull, also called bone material 40, during use to form the counter bore 20 around the pre-existing perforation bore 44. In certain embodiments, the hub 12 in these embodiments is preferably about 13.5 millimeters in diameter and has a depth of about five millimeters in height. Again, the diameter of the hub 12 is such as to be received into the pre-existing perforation bore 44 cut into the cranium, into which the electrodes are inserted. The stated height assures that the bit 2 will be centrally retained in the perforation bore 44 previously cut, and that the ultimate circular milling, also called counter bore 20, is centrally made around that perforation bore 44. In certain embodiments, the shank 4 is about 20 to 25 millimeters in length, terminating at the cutting surface 8 on which flutes are disposed, which surface 8 is about 4 millimeters in depth. In other embodiments, the flutes 10 extend radially outward from hub 12 to a diameter of 23 millimeters (for a Medtronic base and cap) and 29 millimeters (for a MaVigus StimLoc base and cap). Those skilled in the art should recognize that these dimensions are coordinated to the particular drilling tools and implant devices described with the present procedure. It is anticipated that other implant and instrument producers may choose different dimensions for the tools and locking cap 36 that would dictate a change of dimensions to the present invention for compatible use. This adaptability of the present invention increases its impact on the surgical technique in that the tool configuration is so readily adapted to other drivers and fixators.

This patent application expressly incorporates by reference all patents, references, and publications disclosed herein.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A drill bit for cutting a bone, comprising:
   a shaft having a first end and a second end, wherein the first end is adapted to engage a drive so that the shaft rotates;
   a cutting assembly having a plurality of cutting teeth, the cutting assembly attached to the second end of the shaft, wherein the plurality of cutting teeth are planar and extend axially and opposite from the first end of the shaft;
   wherein the cutting assembly is planar and extends radially from the shaft, the cutting assembly having a first side facing the first end of the shaft, the first side of the cutting assembly being opposite of the plurality of cutting teeth;
   wherein the cutting assembly is a solid planar plate extending radially from the shaft for preventing escape of drilled particles therethrough;
   wherein the solid planar plate is structured to provide only a horizontal route of escape for bone residue being cut away from the bone relative to the axis of the shaft such that the continued presence of the bone residue slows the cutting rate of the bit into the bone;
   wherein the plurality of cutting teeth extend a radial length of the cutting assembly in order to define a planar cutting surface; and
   a stabilization hub having an end, the stabilization hub having a consistent diameter, the stabilization hub fixedly attached to the second end of the shaft, wherein the stabilization hub is an axial protuberance of the shaft extending further axially than the plurality of cutting teeth.

2. The drill bit of claim 1, wherein the stabilization hub has a diameter that is less than the diameter of a perforation bore, so that the stabilization hub engages the perforation bore in order to stabilize the location of the cutting assembly.

3. The drill bit of claim 1, wherein the stabilization hub has a diameter less than about 13.5 mm for engaging a perforation bore in order to stabilize the location of the cutting assembly.

4. The drill bit of claim 1, wherein the stabilization hub has a length less than a thickness of a skull, so that the stabilization hub engages only a perforation bore of the skull in order to stabilize the location of the cutting assembly.

5. The drill bit of claim 4, wherein the stabilization hub extends axially from a cutting surface defined by the plurality of cutting teeth a length of from about 5 mm to about 7 mm.

6. The drill bit of claim 1, wherein the end of the stabilization hub is flat.

7. The drill bit of claim 1, wherein the end of the stabilization hub is rounded.

8. The drill bit of claim 1, wherein the plurality of cutting teeth are cutting flutes.

9. A drill bit for cutting bone, comprising:
   a shaft having a first end and a second end, wherein the first end is adapted to engage a drive so that the shaft rotates;
   a plurality of cutting teeth defining a planar cutting surface, each of the plurality having a first end and a second end, each of the first ends fixedly attached to the second end of the shaft, wherein the plurality of cutting teeth extend radially from the shaft;
   wherein each of the plurality of cutting teeth provides a cutting edge at a cutting angle relative to the planar cutting surface which is not perpendicular to the planar cutting surface;
   a planar ring having a first surface, the planar ring fixedly attached to each of the second ends of the plurality of cutting teeth so that the first surface of the planar ring contacts a surface of a cranial bone material in order to obstruct further cutting by the plurality of cutting teeth; and
   a stabilization hub having a consistent diameter fixedly attached to the second end of the shaft, the hub extending axially further than the plurality of cutting teeth, in order to engage a perforation bore in the cranial bone material.

10. The drill bit of claim 9, wherein the first surface of the planar ring has an axial position equal to an axial position of the cutting surface.

11. The drill bit of claim 9, wherein the first surface of the planar ring has an axial position that is about 1 mm recessed from the cutting surface.

12. The drill bit of claim 9, wherein the first surface of the planar ring has an axial position that is about 2 mm recessed from the cutting surface.

13. The drill bit of claim 9, wherein the plurality of cutting teeth is four cutting teeth.

14. The drill bit of claim 9, wherein the planar ring has a diameter of from about 23 mm to about more than 29 mm.

15. The drill bit of claim 9, wherein the width of the planar ring is about 2 mm.

\* \* \* \* \*